United States Patent [19]
Holmes

[11] Patent Number: 6,149,913
[45] Date of Patent: Nov. 21, 2000

[54] COMPOSITIONS AND METHODS FOR CONTROLLING INSECTS

[75] Inventor: Keith Holmes, Cary, N.C.

[73] Assignee: Rhone-Poulenc AG Company, Inc., Research Triangle Park, N.C.

[21] Appl. No.: 09/193,180

[22] Filed: Nov. 16, 1998

[51] Int. Cl.[7] ........................ A61K 35/78; A61K 31/7028
[52] U.S. Cl. ........................ 424/195.1; 424/84; 514/25; 514/341; 514/407; 514/26; 514/33; 514/34
[58] Field of Search ................ 514/25, 341, 407, 514/33, 34, 26; 424/195.1, 84

[56] References Cited

U.S. PATENT DOCUMENTS

| | | | |
|---|---|---|---|
| 4,647,570 | 3/1987 | Shiokawa et al. | 514/341 |
| 4,742,060 | 5/1988 | Shiokawa et al. | 514/252 |
| 4,772,620 | 9/1988 | Shiokawa et al. | 514/341 |
| 4,774,247 | 9/1988 | Shiokawa et al. | 514/256 |
| 4,803,277 | 2/1989 | Shiokawa et al. | 546/264 |
| 4,806,553 | 2/1989 | Shiokawa et al. | 514/332 |
| 4,812,454 | 3/1989 | Shiokawa et al. | 514/256 |
| 4,849,432 | 7/1989 | Shiokawa et al. | 514/341 |
| 4,880,624 | 11/1989 | Metcalf et al. | 424/84 |
| 4,914,113 | 4/1990 | Shiokawa et al. | 514/333 |
| 4,918,086 | 4/1990 | Gsell | 514/351 |
| 4,918,088 | 4/1990 | Gsell | 514/357 |
| 4,948,798 | 8/1990 | Gsell | 514/275 |
| 4,963,572 | 10/1990 | Gsell | 514/357 |
| 4,963,574 | 10/1990 | Bachmann et al. | 514/357 |
| 5,034,404 | 7/1991 | Uneme et al. | 514/365 |
| 5,034,524 | 7/1991 | Shiokawa et al. | 544/124 |
| 5,039,686 | 8/1991 | Davies et al. | 514/341 |
| 5,049,571 | 9/1991 | Gsell | 514/345 |
| 5,063,236 | 11/1991 | Gsell | 514/318 |
| 5,120,540 | 6/1992 | Doane et al. | 424/195.1 |
| 5,232,940 | 8/1993 | Hatton et al. | 514/407 |
| 5,236,938 | 8/1993 | Huang et al. | 514/341 |
| 5,464,618 | 11/1995 | Doane et al. | 424/195.1 |
| 5,484,587 | 1/1996 | Branly et al. | 424/84 |
| 5,571,522 | 11/1996 | Munson et al. | 424/410 |
| 5,707,638 | 1/1998 | Lösel et al. | 424/407 |
| 5,767,137 | 6/1998 | Uhr et al. | 514/360 |
| 5,849,320 | 12/1998 | Turnblad et al. | 424/410 |

FOREIGN PATENT DOCUMENTS

| | | |
|---|---|---|
| 2066405 | 1/1992 | Canada . |
| 0135956 | 4/1985 | European Pat. Off. . |
| 0189972 | 8/1986 | European Pat. Off. . |
| 0192060 | 8/1986 | European Pat. Off. . |
| 0212600 | 3/1987 | European Pat. Off. . |
| 0235725 | 9/1987 | European Pat. Off. . |
| 0154178 | 10/1987 | European Pat. Off. . |
| 0254859 | 2/1988 | European Pat. Off. . |
| 0259738 | 3/1988 | European Pat. Off. . |
| 0295117 | 12/1988 | European Pat. Off. . |
| 0302389 | 2/1989 | European Pat. Off. . |
| 0302833 | 2/1989 | European Pat. Off. . |
| 0303570 | 2/1989 | European Pat. Off. . |
| 0306696 | 3/1989 | European Pat. Off. . |
| 0315826 | 5/1989 | European Pat. Off. . |
| 0163855 | 6/1989 | European Pat. Off. . |
| 0364844 | 4/1990 | European Pat. Off. . |
| 0375907 | 7/1990 | European Pat. Off. . |
| 0383091 | 8/1990 | European Pat. Off. . |
| 0385809 | 9/1990 | European Pat. Off. . |
| 0386565 | 9/1990 | European Pat. Off. . |
| 0403300 | 12/1990 | European Pat. Off. . |
| 0425978 | 5/1991 | European Pat. Off. . |
| 0428941 | 5/1991 | European Pat. Off. . |
| 0455000 | 11/1991 | European Pat. Off. . |
| 0464830 | 1/1992 | European Pat. Off. . |
| 0471372 | 2/1992 | European Pat. Off. . |
| 0679650 | 11/1995 | European Pat. Off. . |
| 3639877 | 5/1988 | Germany . |
| 3712307 | 10/1988 | Germany . |
| 19511269 | 10/1995 | Germany . |
| 63-287764 | 5/1987 | Japan . |
| 63-307857 | 6/1987 | Japan . |
| 2-207083 | 2/1989 | Japan . |
| 3-220176 | 1/1990 | Japan . |
| 3-246283 | 2/1990 | Japan . |
| 3-279359 | 3/1990 | Japan . |
| 3-255072 | 5/1990 | Japan . |
| 87/03781 | 7/1987 | WIPO . |
| 91/04965 | 4/1991 | WIPO . |
| 91/17659 | 11/1991 | WIPO . |
| 93/06089 | 4/1993 | WIPO . |
| 94/21606 | 9/1994 | WIPO . |
| 97/24032 | 7/1997 | WIPO . |

OTHER PUBLICATIONS

*Agricultural Research*, Oct. 1997, pp. 4–7.
*Agricultural Research*, Jan. 1996, pp. 20–22.
www.ars.usda.gov/is/cgi–bin/ffp.pl/is/AR/archive/may98/root0598.htm? cucurbitacin,"Corn Rootworms Get Juiced" (Nov. 9, 1998).
www.psu.edu/ur/NEWS/news/insectACS.html, "Insect Taste Buds Target of Control Method," Mar. 30, 1998 (Nov. 11, 1998).
Derwent WPI Acc No. 89–093657 (1989), abstract of BR 8803621 and patent family list.3/.
Derwent WPI Acc No. 88–252222 (1988), abstract of FR 2611114 and patent family list.4l.

*Primary Examiner*—Francisco Prats
*Attorney, Agent, or Firm*—Burns, Doane, Swecker & Mathis, L.L.P.

[57] ABSTRACT

Compositions and methods for controlling the population of insects are disclosed. The compositions include a feeding stimulant for a particular insect, an effective amount of a 1-arylpyrazole or nicotinyl insecticide to kill an desired insect, at a concentration which is not typically toxic when applied to a plant in the absence of a feeding stimulant and the insect consumes an ordinary amount of toxin during the course of normal feeding, but is toxic when applied in conjunction with a feeding stimulant which causes the insect to consume more of the toxin than would normally be consumed during normal feeding. The use of normally non-toxic amounts of insecticides allows one to minimize the residual insecticide present on the crops. Also, by using a selective feeding stimulant along with a normally non-lethal concentration of insecticide, beneficial insects which are not attracted to the feeding stimulant are not effectively killed off, and detrimental insects which are attracted to the feeding stimulant are effectively killed off.

13 Claims, No Drawings

COMPOSITIONS AND METHODS FOR CONTROLLING INSECTS

The present invention relates to a method of controlling insects at a locus and an insecticidal composition.

BACKGROUND OF THE INVENTION

Farmers growing crops such as cotton, corn and rice commonly use insecticides, and in particular, adulticides, to control the population of detrimental insects, and to minimize the damage caused by the insects. Insecticides are often applied to the soil to kill larvae, or sprayed on the plants to kill the adult insects.

Farmers need to use insecticides in order to grow enough crops to feed the ever increasing population with the ever decreasing amount of available farmland. However, even though food prices would significantly escalate, and food would undoubtedly become scarce without the use of insecticides, the widespread use of insecticides has been opposed because of actual and perceived detrimental environmental and health problems. These problems include the contamination of groundwater and the actual or perceived toxicity of food products containing residual insecticides.

Efforts have been made to increase the effectiveness and selectivity of insecticidal compositions. One method which has been developed involves combining insecticides with bait formulations, typically including insect attractants such as pheromones. In theory, less insecticide is used, and over a narrower area, because the insects are attracted to a specified location. These attractants are more or less efficacious in their attractant power, and help with the selectivity of the insecticide toward harmful rather than beneficial insects. However, a limitation of this approach is that the attractive power of the attractant is generally insufficient for non-confined areas such as crop fields.

It would be advantageous to provide compositions and methods which can lower the residue on crops, and which can be applied to the crops rather that in non-confined areas. For health reasons as well as marketing reasons, there remains a desire to provide insecticidal compositions and methods of using same that provide even less residue than the most effective insecticides to date. The present invention provides such compositions and methods.

SUMMARY OF THE INVENTION

Compositions and methods for controlling a population of insects at a crop locus are disclosed. The compositions include a feeding stimulant (also known as a gustatory stimulant) for the insect to be controlled, a 1-arylpyrazole and/or nicotinyl insecticide and optionally but preferably an adherent, such as a thixotropic agent and/or a carrier. The composition of the invention is advantageously non-solid, preferably liquid or gel-like.

DETAILED DESCRIPTION OF THE INVENTION

Compositions and methods for controlling a population of insects at a crop locus are disclosed. The compositions include a feeding stimulant (also known as a gustatory stimulant) for the insect to be controlled, a 1-arylpyrazole and/or nicotinyl insecticide and optionally but preferably an adherent, such as a thixotropic agent and/or a carrier. The composition of the invention is advantageously non-solid, preferably liquid or gel-like. Viscous compositions are preferred so that they may remain for extended periods of time. Thixotropic compositions are more preferred so that may be applied in a uniform way and remain on the leaves thereafter.

In general, the viscosity of the composition is between about 10 and 20000 centipoise, preferably between about 500 and 12000 centipoise. The viscosities are Brookfield viscosities measured with a viscosimeter in the form of a flat palate rotating at 20 rounds per minute.

The composition typically includes between 0.1 and 40%, preferably between about 2 and 20% by weight of a feeding stimulant, and an insecticide in the range of between 0.0001 and 40%, preferably 0.1 to 5% by weight of the composition. The concentration of the components in the composition is controlled to provide a concentration of insecticide when applied to a crop locus, for example, by aerial application. Useful concentrations of insecticide are typically less than 10 grams/hectare (g/ha), preferably less than 5 g/ha, and more preferably, between 10 and 100 mg/ha. The ratio of feeding stimulant to insecticide in the composition is between 150,000:1 to 10:1, preferably about 40,000:1.

In one embodiment, the concentration of the feeding stimulant in the composition is between approximately 10 and 150 g/liter, preferably between approximately 40 and 60 g/liter, and more preferably, about 50 g/liter. The concentration of the insecticide in the composition is between approximately 1 mg and 1 g/liter, preferably between approximately 1 mg and 500 mg/liter, and more preferably, 1 mg and 10 mg/liter. The composition is applied to the crop locus at a concentration of between about 5 and 15, more preferably, between about 8 and 12, and more preferably, between about 9 and 11 liters/ha, which provides the crop with the necessary levels of feeding stimulant and insecticide.

The insecticides are applied at a concentration which is not typically toxic when applied to a plant in the absence of a feeding stimulant and the insect consumes an ordinary amount of toxin during the course of normal feeding, but is toxic when applied in conjunction with a feeding stimulant which causes the insect to consume more of the toxin than would normally be consumed during normal feeding. The use of normally non-toxic amounts of insecticides allows one to minimize the residual insecticide present on the crops. Also, by using a selective feeding stimulant along with a normally non-lethal concentration of insecticide, beneficial insects which are not attracted to the feeding stimulant are not effectively killed off, and detrimental insects which are attracted to the feeding stimulant are effectively killed off.

DEFINITIONS

The following definitions are provided below to better describe the subject matter being claimed.

As used herein, alkyl radicals and alkyl portions of haloalkyl, haloalkoxy, alkylamino and dialkylamino radicals can have up to seven carbon atoms but are preferably lower alkyl, that is to say, they preferably each have one to four carbon atoms. In the case of the dialkylamino radicals, the alkyl portions can be the same or different.

As used herein, the term "carrier" means any substance used to dilute the insecticide/feeding stimulant prior to application.

I. Compositions

A. Feeding Stimulant

A feeding stimulant is a compound which induces an insect to feed on the composition and preferably to consume an amount of the composition which is on average two times, preferably five times the normal amount of food eaten during the same period of time by the same insect. As the insecticide is present along with the feeding stimulant, at least two to five times the normal amount of insecticide are consumed by the animal.

Many insects are attracted to sweet compounds, such as glucose, fructose, and sucrose. However, insects such as members of *Diabrotica spp.* (e.g., corn rootworm beetles) are attracted to bitter substances known as cucurbitacins. These substances repel most beneficial insects, and tend to attract many deleterious insects.

Suitable feeding stimulants for members of *Diabrotica spp.* include cucurbitacins or sugar derivatives thereof. These materials are generally found in powdered cucurbitacae plants from the genus Cucurbita, and family Cucurbitacaea, which generally includes cucumbers, squash, gourds, watermelons, and cantaloupe. Specific varieties of cucurbits include *Cucurbita foetidissima, Cucurbita ecuadorensis, Cucurbita martenzii, Cucurbita palmeri, Cucurbita pedatifolia, Cucurbita palmata* and *Cucurbita okeechobeensis*.

Suitable cucurbitacins can be extracted using solvents or prepared by milling dried plant matter. Effective derivatives of these substances have been prepared, which are selected for their increased ability to attract insects, and also which are designed to be less water soluble, therefore assisting in keeping the substances on the crop locus for a longer period of time. Cucurbitacin E-glycoside is particularly preferred.

For fire ants, suitable feeding stimulants include vegetable oils and other alkanes. Fire ants are so attracted to corn oil, that a composition including corn oil and Fipronil can be applied to a field infested with fire ants at a concentration of about 20 mg/ha and substantially eliminate virtually all of the fire ants in the field. With respect to fire ants, other vegetable oils, such as palm oil, coconut oil, sesame oil, peanut oil and the like can also be used in place of corn oil. By the term substantially eliminate is meant greater than 80 percent, preferably greater than 90 percent, and more preferably, greater than 95 percent of the ants in the field.

The compositions and methods described herein are effective to control fire ants are generally effective to control both single and multiple queen colonies, the latter being a particularly difficult colony to control with current insecticides.

B. 1-Aryl Pyrazole

Insecticidal 1-arylpyrazoles are known to those of skill in the art. Suitable 1-arylpyrazole or nicotinyl insecticides are those which would normally be effective for the particular insect to be controlled at concentrations of between approximately 10 and 500 g/ha without the added feeding stimulant, and which are effective at concentrations less than 10 g/ha, preferably less than 5 g/ha, and, more preferably, between approximately 10 and 950 mg/ha when combined with the feeding stimulant. Those of skill in the art are either well aware of the effective concentration of the various 1-aryl insecticides to kill a desired pest, or this type of information can readily be determined using no more than routine experimentation.

Preferably, the 1-arylpyrazole has the following formula:

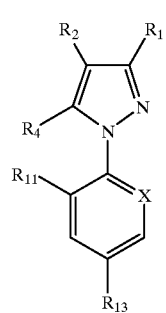

(I)

wherein:
$R_1$ is CN or methyl;
$R_2$ is $S(O)_n R_3$;
$R_3$ is alkyl or haloalkyl;
$R_4$ is H, halo, or a radical selected from $-NR_5 R_6$, $C(O)OR_7$, $-S(O)_m R_7$, alkyl, haloalkyl, $-OR_8$, or $-N=C(R_9)(R_{10})$;
$R_5$ and $R_6$ are independently H, alkyl, haloalkyl, $-C(O)$alkyl, or $-S(O)_r CF_3$; or $R_5$ and $R_6$ form together a divalent radical which may be interrupted by one or more heteroatoms;
$R_7$ is alkyl or haloalkyl;
$R_8$ is H, alkyl, or haloalkyl;
$R_9$ is H or alkyl;
$R_{10}$ is phenyl or heteroaryl, optionally substituted with one or more functional groups selected from hydroxy, halo, $-O$-alkyl, $-S$-alkyl, cyano, alkyl or combinations thereof;
X is N or the radical $C-R_{12}$;
$R_{11}$ and $R_{12}$ are, independently, H or halo.
$R_{13}$ is halo, haloalkyl, haloalkoxy, $-S(O)_q CF_3$ or $-SF_5$;
m, n, q, r are independently 0, 1 or 2;
provided that when $R_1$ is methyl, $R_3$ is haloalkyl, $R_4$ is $NH_2$, $R_{11}$ is Cl, $R_{13}$ is $CF_3$, and X is N.

The alkyl and alkoxy groups of the formula (I) are preferably lower alkyl and alkoxy groups, that is, radicals having one to four carbon atoms. The haloalkyl and haloalkoxy groups likewise preferably have one to four carbon atoms. The haloalkyl and haloalkoxy groups can bear one or more halogen atoms; preferred groups of this type include $-CF_3$ and $-OCF_3$.

Preferably, the 1-arylpyrazole has the following substitution:
$R_1$ is CN; and/or $R_4$ is $-NR_5 R_6$; and/or $R_5$ and $R_6$ are independently H, alkyl, haloalkyl, $-C(O)$alkyl, or $-C(O)OR_7$; and/or X is $C-R_{12}$; and/or $R_{13}$ is halo, haloalkyl, haloalkoxy, or $-SF_5$.

The most preferred 1-arylpyrazole is 5-amino-3-cyano-1-(2,6-dichloro-4-trifluoromethylphenyl)-4-trifluoromethylsulfinylpyrazole (Fipronil).

The compounds of formula (I) can be prepared using techniques known to those of skill in the art, including for example, processes disclosed in International Patent Publications No. WO 87/03781, WO 93/06089 and WO 94/21606, as well as in European Patent Publication numbers 0295117, 0403300, 0385809, and 0679650, German Patent Publication 19511269 and U.S. Pat. Nos. 5,232,940 and 5,236,938.

C. Nicotinyl Insecticide

Nicotinyl insecticides are known to those of skill in the art, and are commonly known as agonists or antagonists of acetylcholine receptors. Suitable nicotinyl insecticides are those which would normally be effective for the particular insect to be controlled at concentrations of between approximately 10 and 500 g/ha without the added feeding stimulant, and which are effective at concentrations less than 10 g/ha, preferably less than 5 g/ha, and, more preferably, between approximately 10 and 950 mg/ha when combined with the feeding stimulant. Those of skill in the art are either well aware of the effective concentration of the various nicotinyl insecticides to kill a desired pest, or this type of information can readily be determined using no more than routine experimentation.

The use of NI25 is specifically hereby disclaimed. This disclaimer is not being made for reasons of prior art.

Examples of agonists and antagonists of the nicotinergic acetylcholine receptors are those disclosed in European Patent Application Nos. 464,830, 428,941, 425,978, 386, 565, 383,091, 375,907, 364,844, 315,826, 259,738, 254,859, 235,725, 212,600, 192,060, 163,855, 154,178, 136,686, 303, 570, 302,833, 306,696, 189,972, 455,000, 135,956, 471,372, and 302,389; German Application Nos. 3,639,877, 3,712, 307; Japanese Application Nos. 03,220,176, 02,207,083, 63,307,857, 63,287,764, 03,246,283, 03,279,359, and 03,255,072; U.S. Pat. Nos. 5,034,524, 4,948,798, 4,918,086, 5,039,686, and 5,034,404; PCT applications WO 91/17659 and 91/4965; French application 2,611,114; and Brazilian application 88 03 621, which have the effectiveness described above.

These compounds are described as a group having the name nitromethylenes and related compounds. These compounds may preferably be described by the general structure

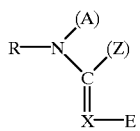

(II)

wherein:

R is hydrogen, optionally substituted acyl, alkyl, aryl, aralkyl, heteroaryl, or heteroarylalkyl;

A is a monofanctional group selected from H, acyl, alkyl, aryl, or bifunctional groups attached to the Z remainder;

E is an electron-attracting remainder;

X' is the remainder —CH= or =N— where the —CH= remainder instead of an H atom can be attached to the Z remainder;

Z is a mono functional group selected from alkyl, —OR, —SR,

or bifunctional groups which are attached to the A remainder or to the X remainder.

Preferably, the compounds of Formula II have the following substitutions:

R is H or optionally substituted remainders selected from acyl, alkyl, aryl, aralkyl, heteroaryl or heteroarylalkyl.

Suitable acyl remainders include formyl, alkylcarbonyl, arylcarbonyl, allylsulfonyl, arylsulfonyl, and (alkyl-)-(aryl-)-phosphoryl, which in turn can be substituted. Suitable alkyls are $C_1$–$C_{10}$ alkyl, in particular $C_1$–$C_4$ alkyl, specifically methyl, alkyl, i-propyl, sec.- or t-butyl, which in turn can be substituted. Suitable aryls include phenyl and naphthyl, most preferably, phenyl. Suitable aralkyls include phenylrnethyl and phenethyl. Suitable heteroaryls include heteroaryls having up to 10 ring atoms and N, O, S, in particular, N, as the hetero atoms. Examples include thiophenyl, firryl, thiazolyl, imidazolyl, pyridyl, and benzthiazolyl. Suitable heteroarylalkyls include heteroarylmethyl, heteroarylethyl having up to 6 ring atoms and N, O, S, in particular, N, as hetero atoms.

Preferably, the alkyl groups have between 1 and 4, more preferably between 1 and 2 carbon atoms, such as methyl, ethyl, n- and i-propyl and n-, i- and t-butyl. Alkoxy groups preferably have been 1 and 4, more preferably between 1 and 2 carbon atoms, such as methoxy, ethoxy, n- and i-propyloxy, and n-, i- and t-butyloxy. Alkylthios preferably have between 1 and 4, more preferably between 1 and 2 carbon atoms, such as methylthio, ethylthio, n- and i-propylthio and n-, i- and t-butylthio. Haloalkyls preferably have between 1 and 4, more preferably between 1 and 2 carbon atoms, and preferably between 1 and 5, more preferably, between 1 and 3 halogen atoms, wherein the halogen atoms are the same or different, and preferably are fluorine, chlorine, or bromine, more preferably fluorine. An example of a preferred haloalkyl group is trifluoromethyl.

Suitable optional substituents include hydroxy; halo, preferably fluoro, chloro, or bromo, cyano; nitro; amino; monoalkyl and dialkylaminos preferably having between 1 and 4, more preferably between 1 and 2 carbon atoms per alkyl group, for example, methylamino, ethylamino, n- and i- propylamino and methyl-n-butylamino; carboxyls; carbalkoxys preferably having between 2 and 4, more preferably between 2 and 3 carbon atoms, such as carbomethoxy and carboethoxy; sulfo (—$SO_3H$); alkylsulfonyl, preferably having between 1 and 4, more preferably between 1 and 2 carbon atoms, such as methylsulfonyl and ethylsulfonyl; arylsulfonyl preferably having 6 or 10 aryl carbon atoms, such as phenylsulfonyl, and heteroarylamino and heteroarylalkylamino such as chloropyridylamino and chloropyridylmethylamino.

A is H or optionally substituted remainders selected from acyl, alkyl, or aryl, which preferably have the meanings stated above. A also stands for a bifunctional group. Typical examples are optionally substituted alkylene groups having between 1 and 4, more preferably between 1 and 2 carbon atoms.

A and Z, together with the atoms to which they are bonded, may form a saturated or unsaturated heterocyclic ring. The heterocyclic ring may contain one or two identical or different hetero atoms and/or hetero groups. Preferable hetero atoms are oxygen, sulfur, or nitrogen; typical hetero groups are N-alkyl, where the alkyl of the N-alkyl group preferably contains between 1 and 4, more preferably between 1 and 2 carbon atoms. Typical alkyls are methyl, ethyl, n- and i-propyl and n-, i- and t-butyl. The heterocyclic ring contains between 5 and 7, preferably five or six ring members. Examples of suitable heterocyclic rings include pyrrolidine, piperidine, piperazine, hexamethylenimine, morpholine, and N-methylpiperazine.

E is an electron-attracting remainder, in particular $NO_2$, CN, haloalkyl carbonyl as well as 1,5-halogen-$C_1$–$C_4$-carbonyl, in particular $C(O)CF_3$.

X is —CH= or —N=

Z is an optionally substituted remainder selected from alkyl, —OR, —SR, or —NRR, wherein R and the substituents have the meaning stated above.

Z can form a saturated or unsaturated heterocyclic ring at the position of X together with the atom to which it is attached and the remainder

The heterocyclic ring can contain an additional one or two identical or different hetero atoms and/or hetero groups. The hetero atoms are preferably oxygen, sulfur, or nitrogen, and the hetero groups are N-alkyl, where the alkyl or N-alkyl group preferably contains between 1 and 4, more preferably between 1 and 2 carbon atoms. Preferred alkyls are methyl, ethyl, n- and i-propyl, and n-, i-, and t-butyl. The heterocyclic ring contains between 5 and 7, preferably between 5 and 6 ring members. Suitable examples of heterocyclic rings include pyrrolidine, piperidine, piperazine, hexamethylenediamine, morpholine, and N-methylpiperazine.

The agonists and antagonists of the nicotinergic acetylcholine receptors are preferably compounds having the following structure:

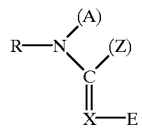

wherein:

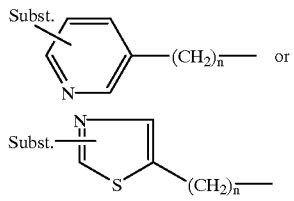

n is 1 or 2,

Subst. stands for one of the substituents listed above, preferably, halogen, more preferably, chlorine, and A, Z, X, and E have the meanings stated above.

Specifically, the following compounds are cited:

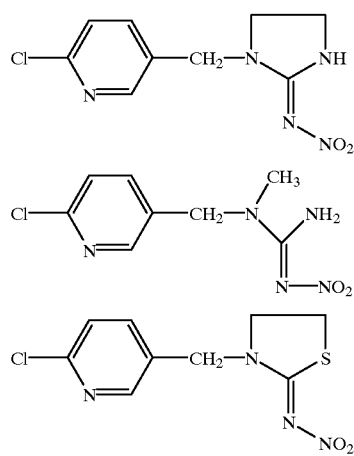

-continued

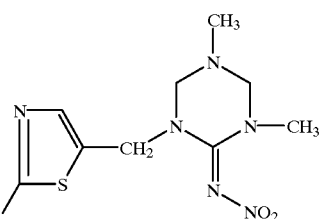

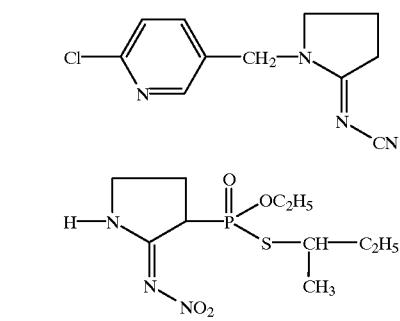

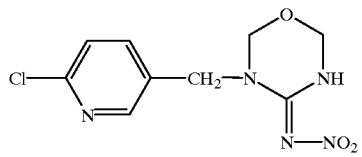

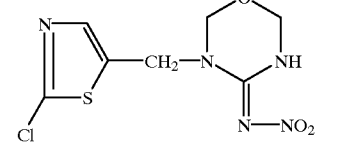

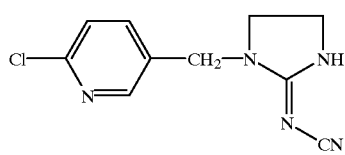

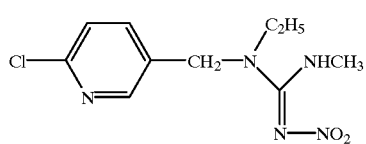

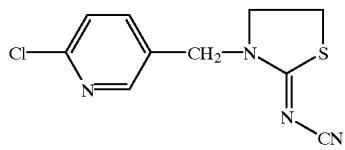

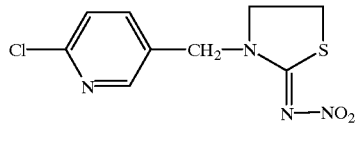

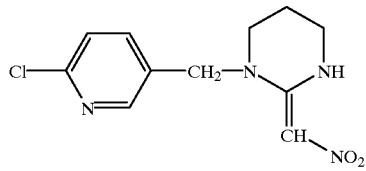

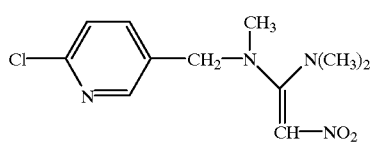
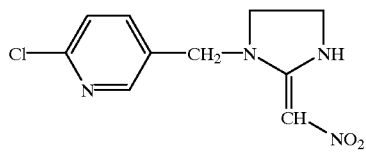
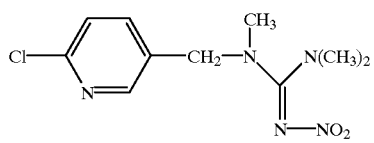
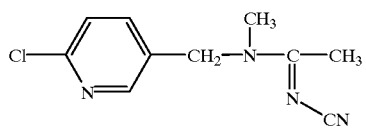
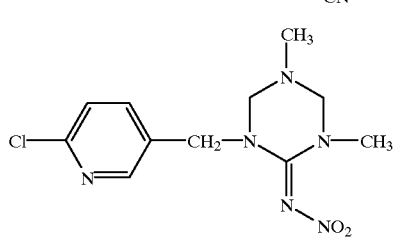
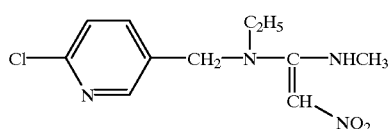
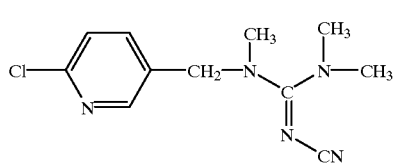
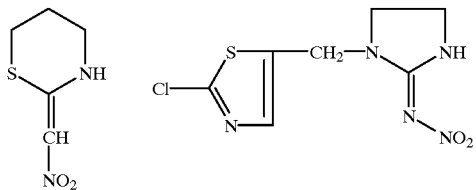
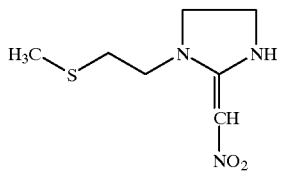
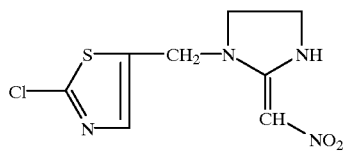
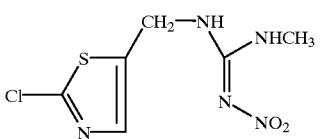
Especially preferred agonists and antagonists of the nicotinergic acetylcholine receptors are compounds having the structures:
(IIa)
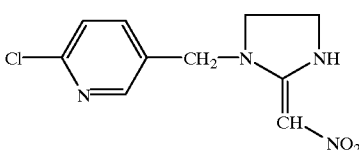
(IIb)
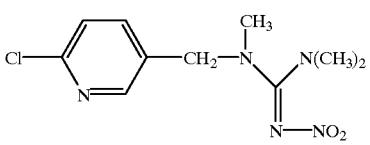
(IIc)
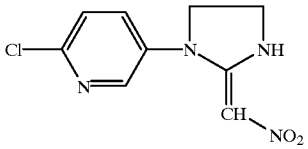
(IId)
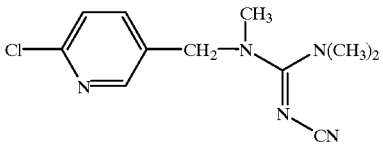
(IIe)
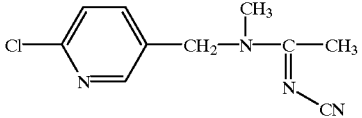
(IIf)
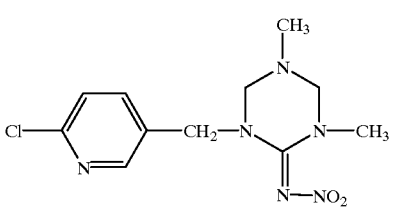
(IIg)
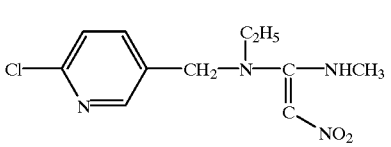

-continued

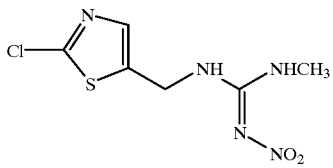

(IIh)

in particular compounds having the structure

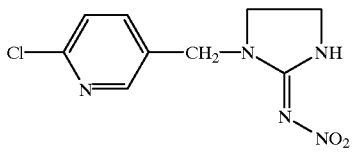

(IIi)

The most preferred compounds in this class are imidacloprid and thiomethoxam.

D. Adherents

Adherents are materials which cause the insecticidal composition to adhere to the crop once it is administered, and remain for an extended period of time without being washed away by water. Suitable adherents include polymers such as polybutadiene and copolymers thereof, i.e., polybutadiene/styrene copolymers, as well as thixotropic agents. Adherents are commercially available in different viscosities, which are appropriate for different applications. For example, the location of use, the type of crop being treated, the temperature and time of use, and the weather conditions in the crop locus, are examples of factors which might be taken into consideration when selecting an appropriate adherent.

Thixotropic agents are materials which are solid or gel-like when not subjected to mechanical stress, but which liquefy upon exposure to mechanical stress. These can be preferred when the composition is administered in a manner which induces mechanical stress, for example, by aerial application. When the aerial application is performed, mechanical stress used to form appropriately sized droplets of the composition induces sufficient mechanical stress to liquefy the composition. The contact of the drops with the crop also may liquefy the composition. However, in the absence of mechanical stress, the composition re-gels or re-solidifies, and thereby adheres to the crop. Suitable thixotropic agents are known to those of skill in the art, and are described, for example, in Canadian Patent No. 2066405, the contents of which are hereby incorporated by reference.

Because the feeding stimulant and insecticide may both be water soluble, the presence of a thixotropic agent can be preferred to provide the compositions with the ability to remain on the crops to which they are applied for a sufficient period of time to effectively kill a significant percentage of the insect population.

E. Carrier

The composition is preferably in the form of a gel, a dispersion, an emulsion, or a solution, which optionally incorporates various wetting, dispersing, emulsifying or gelling agents, such as thixotropic agents.

Suitable wetting, dispersing and emulsifying agents include sulphoricinoleates, quaternary ammonium derivatives or products based upon condensates of ethylene oxide with nonyl- and octylphenol, or carboxylic acid esters of anhydrosorbitols which have been rendered soluble by etherification of the free hydroxy groups by condensation with ethylene oxide, or mixtures of these types of agents. Wettable powders may be treated with water immediately before use to give suspensions ready for application.

These gels, emulsions, suspensions, dispersions, and/or solutions may be prepared using aqueous, organic or aqueous-organic diluents, for example acetophenone, isophorone, toluene, xylene, mineral, animal or vegetable oils, and water soluble polymers (and mixtures of these diluents), which may contain wetting, dispersing or emulsifying agents of the ionic or non-ionic types or mixtures thereof, for example those of the types described above. When desired, the emulsions containing the feeding stimulant and insecticide may be used in the form of self-emulsifying concentrates containing the active substance dissolved in the emulsifying agents or in solvents containing emulsifying agents compatible with the active substance, the simple addition of water to such concentrates producing compositions ready for use.

The compositions are preferably present as liquid concentrates, or as gel-like materials, which are capable of being applied via aerial application equipment. Liquid compositions include water miscible concentrates, emulsifiable concentrates, flowable suspensions, and wettable or soluble powders, although the materials are preferably present in the form of a thixotropic gel.

Compositions in the form of aerosols and aqueous or non-aqueous solutions or dispersions suitable for spraying, fogging and low- or ultra-low volume spraying may also be used.

F. Optional Components

The compositions can include as optional components additives such as adjuvants, carriers, wetting agents, surfactants, dispersants, dye-stuffs, thixotropic agents, and preferably sticking agents or adhesives or glues. The compositions can also optionally include stabilizing substances, other insecticides, acaricides, plant nematocides, anthelmintics or anticoccidials, fungicides (agricultural or veterinary as appropriate e.g. benomyl, iprodione), bactericides, and various insect attractants, repellents or pheromones. These may be designed to improve potency, persistence, safety, uptake where desired, spectrum of insects controlled or to enable the composition to perform other useful functions in the same area treated.

II. Insects Which Can Be Controlled

The compositions and methods described herein are effective at eliminating or substantially reducing the population of a large variety of insects, for example, including adults, larvae and eggs of Lepidoptera (butterflies and moths), e.g. *Heliothis spp.* such as *Heliothis virescens* (tobacco budworm), *Heliothis armioera* and *Heliothis zea, Spodoptera spp.* such as *S exempta, S. littoralis* (Egyptian cotton worm), *S. eridania* (southern army worm), *Mamestra configurata* (bertha army worm); *Earias spp.* e.g. *E. insulana* (Egyptian bollworm), *Pectinophora spp.* e.g. *Pectinophora gossypiella* (pink bollworm), *Ostrinia spp.* such as *O. nubilalis* (European comborer), *Trichoplusia ni* (cabbage looper), *Pieris spp.* (cabbage worms), *Laphyqma spp.* (army worms), *Agrotis* and *Amathes spp.* (cutworms), *Wiseana spp.* (porina moth), *Chilo spp.* (rice stem borer), *Tryporyza spp.* and *Diatraea spp.* (sugar cane borers and rice borers), *Sparganothis pilleriana* (grape berry moth), *Cydia pomonella* (codling moth), *Archips spp.* (fruit tree tortrix moths), *Plutella xylostella* (diamond back moth); against adult and larvae of Coleoptera (beetles) e.g. *Hypothenemus hampei* (coffee berry borer), *Hylesinus spp.* (bark beetles), *Anthonomus grandis* (cotton boll weevil), *Acalymma spp.*

(cucumber beetles), *Lema spp., Psylliodes spp., Leptinotarsa decemlineata* (Colorado potato beetle), *Diabrotica spp.* (corn rootworms), *Gonocephalum spp.* (false wire worms), *Agriotes spp.* (wireworms), *Dermolepida* and *Heteronychus spp.* (white grubs), *Phaedon cochleariae* (mustard beetle), *Lissorhoptrus oryzophilus* (rice water weevil), *Melioethes spp.* (pollen beetles), *Ceutorhynchus spp., Rhynchophorus* and *Cosmopolites spp.* (root weevils); against Hemiptera e.g. *Psylla spp., Bemisia spp., Trialeurodes spp., Aphis spp., Myzus spp., Megoura viciae, Phylloxera spp., Adelges spp., Phorodon humuli* (hop damson aphid), *Aeneolamia spp., Nephotettix spp.* (rice leaf hoppers), *Empoasca spp., Nilaparvata spp., Perkinsiella spp., Pyrilla spp., Aonidiella spp.* (red scales), *Coccus spp., Pseucoccus spp., Helopeltis spp.* (mosquito bugs), *Lygus spp., Dysdercus spp., Oxycarenus spp., Nezara spp.;* Hymenoptera e.g. *Athalia spp.* and *Cephus spp.* (saw flies), *Atta spp.* (leaf cutting ants); *Diptera e.g. Hylemyia spp.* (root flies), *Atherigona spp., Chlorops spp.* (shoot flies), *Phytomyza spp.* (leaf miners), *Ceratitis spp.* (fruit flies); Thysanoptera such as *Thrips tabaci:* Orthoptera such as *Locusta* and *Schistocerca spp.* (locusts) and crickets e.g. *Gryllus spp.* and *Acheta spp.*; Collembola e.g. *Sminthurus spp.* and *Onychiurus spp.* (springtails), Isoptera e.g. *Odontotermes spp.* (termites), Dermaptera e.g. *Forficula spp.* (earwigs) and also other arthropods of agricultural significance such as Acari (mites) e.g. *Tetranychus spp., Panonychus spp. and Bryobia spp.* (spider mites), *Eriophyes spp.* (gall mites), *Polyphacotarsonemus spp.; Blaniulus spp.* (millipedes), *Scutigerella spp.* (symphilids), *Oniscus spp.* (woodlice) and *Triops spp.* (crustacea).

Suitable feeding stimulants for these insects are either known or can be determined through no more than routine experimentation.

Specific insects which are currently problematic in corn, cotton, and rice crops, as well as fire ants, which are problematic throughout the country, will be discussed in more detail below.

A. Diabrotica

One example of pest which can be controlled using the compositions and methods disclosed herein include corn and vegetable-destroying pests, generally beetles, especially pests of the class Diabrotica, more particularly *Diabrotica virgifera, Diabrotica undecimpunctata undecimpunctata, Diabrotica undecimpunctata howardi, Diabrotica balteata, Diabrotica decolor, Diabrotica duodecimpunctata, Diabrotica longicornis, Diabrotica vittata.* The method of control is especially preferred for controlling adult pests.

B. FireAnts

Fire ants are common in the United States as well as around the world. Their bite is harmful to humans, causing pain to those bitten by them. Currently, there are not believed to be generally effective means for eradicating fire ants from a domestic locus or a crop locus. Typical methods for killing fire ants include spraying a liquid insecticidal composition directly on an ant hill or by the use of baits. These methods tend to reduce, but not effectively eliminate, the fire ant population.

C. Boll Weevils

Boll weevils are the principle insect responsible for damaging cotton crops. Infestations of boll weevils are often treated by setting up baited traps including Grandlure, the boll weevil pheremone. Grandlure can also optionally be used in connection with the compositions and methods described herein.

III. Methods of Application

The methods of controlling insects at a locus involve administering the composition to a crop locus at a concentration in which the insecticide alone is non-toxic to the insect during normal feeding throughout the entire crop locus when the insect is not otherwise attracted to the insecticide, but is toxic by virtue of the feeding stimulant, which causes the insect to seek out and eat an effective insecticidal amount of the insecticide, even at the extremely low dosages in which it is applied. Preferred methods of applying the composition include crop-dusting and spraying. The preferred droplet size is between 20 and 1000 microns, preferably between 30 and 800 microns, and, most preferably, around 500 microns. Other methods known to those of skill in the art may be used, but are less preferred.

The compositions and methods described herein are of particular value in the protection of field, forage, plantation, orchard and vineyard crops, of ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

For the control of the insects described herein, in particular, insects of the class Diabrotica, fire ants, boll weevils and rice water weevils, the active compound is generally applied to the locus in which infestation is to be controlled at a rate of about 10 mg to about 10 g, preferably between 10 mg and 5 g, and, more preferably, between 10 and 990 mg of active compound per hectare of locus treated. Under ideal conditions, depending on the pest to be controlled, the lower rate may offer adequate protection. On the other hand, adverse weather conditions, resistance of the pest and other factors may require that the active ingredient be used in higher proportions. The actual compositions employed and their rate of application will be selected to achieve the desired effect(s) by the farmer, pest control operator or other person skilled in the art.

For control of Diabrotica, the composition is advantageously administered in a non-solid form, for example, as foliar sprays, dusts, fogs and/or foams, and is preferably able to remain on the leaves during the time pupation and reproduction of an insect. A preferred method for applying the compositions is by aerial application. Methods for aerial application are known to those of skill in the art. When the crop being treated is one which has leaves, the composition is preferably applied on the leaves of the crop or close to the leaves.

For control of fire ants, the composition is advantageously administered in a solid form, particularly a granule that may be broadcast or may be applied as a discrete mound.

The composition is preferably administered at a concentration of about 9 liters per acre, to provide an effective concentration of the insecticide and feeding stimulant. Alternate methods of application include spraying.

The compositions are preferably applied at an optimum time for the particular crop to be treated. Optimum times include when the crop is most susceptible to insect infestation, and also when the insect is most likely to be at a stage of development where it can be most effectively treated with the insecticide/feeding stimulant combination. Preferably, to adequately control a population of insects which undergo pupation and reproduction, and particularly when a thixotropic agent is used, the compositions remain on the crops for a significant amount of time, i.e., greater than 10 days, and, more preferably, between 15 and 50 days.

For this purpose, the active ingredient and the components of the compositions are chosen in such a way that the efficacy or lethal activity of the composition remains more than 15 days, preferably more than 25 days. Some particular circumstances may provide duration of activity outside these ranges. The composition may be applied only during the period of time where the male pests have emerged from pupation and are in circulation, however, it is generally preferred to apply the composition when both males and females are present.

For certain Diabrotica spp., for example, corn rootworm beetles, the adults and larvae are both alive at the same time, and are undergoing cycles of reproduction and pupation, respectively. By applying the composition over the top of the corn plant, the adults which are present at the crop locus are killed. Because the adults are killed, the reproductive cycle of the population is then substantially halted. Accordingly, the entire population of insects, adults and larvae, can be reduced with one insecticidal application. In such an application, it is preferred that the composition remains on the crops for at least fifteen days, and, more preferably, between 25 and 50 days.

For certain crops, for example, cotton, the insects, for example, the boll weevil, tend to cause the most damage at the fruiting stage (often referred to as pinhead square). If the composition is applied to cotton at a time ranging from between the beginning of the fruiting stage to the time of harvest, the composition will be effective at treating the insect infestation throughout a substantial part of the growing season.

The compositions and methods described herein will be better understood with respect to the following non-limiting examples.

EXAMPLE 1

Control of *Diabrotica virgifera* at a Corn Field

The following conditions are applicable when a one hectare field of corn about 1.5 meters high and at the stage of tasseling and silking is invaded by the adults of *Diabrotica virgifera,* which are a variety of corn root beetles. At the beginning of the invasion, the field is sprayed with a sticky gel formulation which includes about 0.01% Fipronil, an adherent described in Canadian Patent 2066405, as well as about 40% of cucurbitacin E-glycoside obtained by extraction of a watermelon. It is sprayed at a dose providing about 0.1 g/ha of Fipronil. The gel sticks to the leaves of the corn plants. After three weeks the population of the beetles is reduced by about 95%.

EXAMPLE 2

Control of Fireants

The following conditions apply to treating a field of pasture about one hectare in area which is infested with fire ants (solenopsis invicta) in multi- and/or single-queen colonies, where ther arre about 300 visible mounds. A granular bait formulation that includes fipronil, corn oil and corn cob is broadcast over the area such that the rate of fipronil is about 20 mg/ha. After one week, there is about a 90% reduction in the number of fire ants.

While the invention has been described in terms of various preferred embodiments, the skilled artisan will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A method of controlling Diabrotica insects at a crop locus or which may invade a crop locus, which comprises applying to the locus a composition comprising:

a) a cucurbitacin feeding stimulant, and b) an amount effective at controlling the diabrotica insect population of an insecticide selected from aryl pyrazole insecticides, said amount being about 0.1 to 0.9 g/ha or less insecticide.

2. The method of claim 1, wherein the composition further comprises an adherent.

3. The method of claim 3, wherein the adherent is a thixotropic agent.

4. The method of claim 1, wherein the composition is in a non-solid form.

5. The method of claim 1, wherein the composition is applied to the crop locus by aerial application.

6. The method of claim 1, wherein the composition remains on the crop locus for a period of time greater than 15 days.

7. The method of claim 1, wherein the feeding stimulant induces the insect to consume between 10 and 150 percent of its body weight of the composition.

8. The method of claim 1, wherein the 1-aryl pyrazole is a compound of the following formula:

(I)

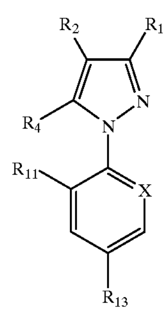

wherein:

$R_1$ is CN or methyl;

$R_2$ is $S(O)_nR_3$;

$R_3$ is alkyl or haloalkyl;

$R_4$ is H, halo, or a radical selected from $-NR_5R_6$, $C(O)OR_7$, $-S(O)_mR_7$, alkyl, haloalkyl, $-OR_8$, or $-N{=}C(R_9)(R_{10})$;

$R_5$ and $R_6$ are independently H, alkyl, haloalkyl, —C(O) alkyl, or $-S(O)_rCF_3$; or $R_5$ and $R_6$ form together a divalent radical which may be interrupted by one or more heteroatoms;

$R_7$ is alkyl or haloalkyl;

$R_8$ is H, alkyl, or haloalkyl;

$R_9$ is H or alkyl;

$R_{10}$ is phenyl or heteroaryl, optionally substituted with one or more functional groups selected from hydroxy, halo, —O-alkyl, —S-alkyl, cyano, alkyl or combinations thereof;

X is N or the radical C-$R_{12}$;

$R_{11}$ and $R_{12}$ are, independently, H or halo, $R_{13}$ is halo, haloalkyl, haloalkoxy, —S(O)$_q$CF$_3$ or —SF$_5$;

m, n, q, r are independently 0, 1, or 2;

provided that when $R_1$ is methyl, $R_3$ is haloalkyl, $R_4$ is NH$_2$, $R_{11}$ is Cl, $R_{13}$ is CF$_3$, and X is N.

9. The method of claim 8, wherein $R_1$ is CN; and/or $R_4$ is —NR$_5$R$_6$; and/or $R_5$ and $R_6$ are independently H, alkyl, haloalkyl, —C(O)alkyl, or C(O)OR$_7$; and/or X is C-R$_{12}$; and/or $R_{13}$ is halo, haloalkyl, haloalkoxy, or —SF$_5$.

10. The method of claim 1, wherein the 1-arylpyrazole is 5-amino-3-cyano-1-(2,6-dichloro-4-trifluoromethylphenyl)-4-trifluoromethylsulfinylpyrazole (Fipronil).

11. The method of claim 1 wherein the cucurbitacin is cucurbitacin E-glycoside.

12. The method of claim 1, wherein the feeding stimulant is cucurbitacin E-glycoside and the insecticide is 5-amino-3-cyano-1-(2,6-dichloro-4-trifluoromethylphenyl)-4-trifluoromethylsulfinylpyrazole.

13. The method of claim 1, wherein the insecticide is effective to provide control of the population of insects during a period of time wherein at least a portion of the population undergoes pupation and reproduction.

* * * * *